United States Patent [19]

Cance et al.

[11] Patent Number: 5,053,491

[45] Date of Patent: * Oct. 1, 1991

[54] MONOCLONAL ANTIBODIES AND CELL LINES FOR PARATHYROID TISSUE-SPECIFIC ANTIGEN

[75] Inventors: William G. Cance; Joseph M. Davie; Samuel A. Wells, Jr.; William G. Dilley; Michael J. Welch; Jeremiah J. Morrissey, IV, all of St. Louis, Mo.

[73] Assignee: Washington University School of Medicine, St. Louis, Mo.

[ * ] Notice: The portion of the term of this patent subsequent to Sep. 5, 2006 has been disclaimed.

[21] Appl. No.: 342,312

[22] Filed: Apr. 24, 1989

Related U.S. Application Data

[63] Continuation of Ser. No. 808,865, Dec. 13, 1985, Pat. No. 4,864,020.

[51] Int. Cl.$^5$ .................... A61K 39/00; A61K 43/00; C12N 5/20; C07K 15/28
[52] U.S. Cl. ..................................... 530/387; 424/1.1; 424/85.8; 424/88; 435/70.21; 435/172.2; 435/240.27; 530/388; 935/104; 935/107; 935/110
[58] Field of Search ......................... 424/1.1, 85.8, 88; 435/70.21, 172.2, 240.27; 530/387-388; 935/100, 104, 107, 108, 110

[56] References Cited

PUBLICATIONS

Scheinberg et al., Science (1982) 215:1511-1513.
Papapoulous et al., Chem. Abstracts (1979) 90(23):291-292.
Hesch et al., Chem. Abstracts (1975) 83(13):268-269.
Cance et al., Proc. Natl. Acad. Sci. (1986)83:6112-6116.
Cance et al., Surgery Forum (1986) 37:410-412.
Posillico et al., J. Clin. Endocrinol. Metabolism (1987), 64(1):43-50.
Srikanta et al., Endocrinol. (1987)120(6):2240-2244.
Nussbaum et al., Chem. Abstracts (1986) 105:1134.
Nussbaum et al., Meth. Enzymol. (1985)109:25-638.
Weinshank et al., Chem. Abstracts (1985)103:Abstract No. 190337f.

*Primary Examiner*—Margaret Moskowitz
*Assistant Examiner*—Robert D. Budens
*Attorney, Agent, or Firm*—Irell & Manella

[57] ABSTRACT

Monoclonal antibodies specific for an antigen present on the surface of parathyroid tissue are useful in imaging such tissue when conjugated to suitable label. The antibodies of the invention bind exclusively to parathyroid surfaces and do not bind to other tissues. The antibodies are useful in establishing the location of the parathyroid whether in its normal location or in ectopic placements. An exemplary monoclonal has been deposited at the American Type Culture Collection and has accession number ATCC No. HB9917.

15 Claims, 4 Drawing Sheets

FIG. 5

MONOCLONAL ANTIBODIES AND CELL LINES FOR PARATHYROID TISSUE-SPECIFIC ANTIGEN

This application is a continuation of application Ser. No. 06/808,865, filed 13 Dec. 1985, now U.S. Pat. No. 4,864,020.

TECHNICAL FIELD

The invention relates to monoclonal antibodies and to techniques for imaging desired target tissue to permit its precise localization. In particular, this invention relates to identifying the location of parathyroid tissue using antibodies, and to the therapeutic use of these antibodies.

BACKGROUND ART

An estimated 250,000 people in the United States exhibit abnormally high secretion of parathyroid hormone, an 84-amino acid linear peptide which is involved in regulating the concentration of calcium ion in the plasma. The hormone apparently acts by regulating bone resorption and tubular reabsorption of calcium and phosphorus in the kidney. In primary hyperparathyroidism, tissue calcium storage is decreased, and bone demineralization results. Generally, hyperparathyroidism is the result of tumor formation in the parathyroid glands, four small egg-shaped glands closely associated with the thyroid.

The standard treatment for hyperparathyroidism is surgical removal of all abnormally enlarged glands. To do so successfully, however, requires that they be precisely located. They are notoriously difficult to locate, and even after surgery, symptoms may persist due to failure to remove hyperfunctioning parathyroid tissue completely.

While the approximate location of the parathyroids is presumed known, precise location is not established, and, further, these glands may be ectopic in various locations in the neck, throat and chest region. Therefore, an imaging technique which would permit the surgeon to establish the location of parathyroid tissue either in normal locations or ectopic placements is highly desirable. Such techniques are not presently available in the art.

Substances specific for parathyroid tissue are useful for development of such techniques. Antibodies, if properly chosen, show the necessary specificity. Monoclonal antibodies reactive with parathyroid tissue have been used to modulate the secretory function (Posillico, J. T., et al, Clin Res (1985) 33:473A. However, these antibodies may not be suitable for imaging.

DISCLOSURE OF THE INVENTION

The invention provides a highly specific imaging technique for visualizing the parathyroid glands prior to surgery. The technique employs a labeled monoclonal antibody preparation which is highly immunoreactive with an antigen associated with parathyroid tissue and which antibody preparation does not react with other types of cells. Administration of this labeled monoclonal antibody prior to surgery permits imaging of the neck, throat and chest area to obtain a clear picture of the location of parathyroid tissue.

In addition, the antibodies of the invention stimulate the secretion of parathyroid hormone and are thus useful in treating patients who exhibit a deficiency in the ability to secrete this hormone, they can also be conjugated to toxic moieties in order to form immunotoxins therapeutically useful in treating hyperplasia of the parathyroid gland.

In one aspect, the invention is directed to monoclonal antibody preparations useful in radioimaging parathyroid tissue. These monoclonal antibodies are specifically reactive with parathyroid tissue to the exclusion of other types, and include monoclonals of the IgM class, but for use in this purpose are preferably preparations comprising IgG antibodies. The invention further includes these antibodies in labeled form. For use in treating hypoparathyroidism, antibodies of class IgM are preferred. Either class may be employed to form immunotoxins. In addition, for use in radioimaging and in the preparation of immunotoxins, fragments of the antibodies which retain antigen specificity may be employed. Accordingly, the Fab or F(ab')$_2$ fragments may also be used for this purpose.

In another aspect, the invention is directed to immortalized cell cultures capable of producing the antibodies of desired specificity. In still another aspect, the invention relates to radioimaging techniques using the antibodies of the invention, to methods of treating hypoparathyroidism with the parathyroid-specific monoclonal antibodies and to methods of treating hyperparathyroidism using immunotoxins prepared from the antibodies of the invention.

MODES OF CARRYING OUT THE INVENTION

A. Definitions

Antibodies "specifically immunoreactive" with a particular antigen refers to the ability to react positively with the antigen to the exclusion of others. It is recognized that at high enough concentration, immunoglobulins in general will bind to substrates nonspecifically. However, this nonspecific binding can be discerned by diluting the sample appropriately and comparing the effects of this dilution to dilutions of a specifically reacting antibody.

A "parathyroid-characteristic antigen" refers to a substance which contains an antigenic determinant found exclusively on parathyroid tissues and not on other tissues derived from the same organism.

The "191 kd" antigen refers to an antigen specifically associated with parathyroid tissue which binds to a specific monoclonal antibody preparation herein (BB5). This antigen shows a molecular weight on SDS-PAGE run in the absence of 2-mercaptoethanol (BME) of 191 kd; in the presence of BME, the apparent molecular weight is 171 kd. The antigen is associated with the parathyroid cell surface and is apparently not secreted.

"Cells", "cell line", and "cell cultures" are generally used interchangeably, unless otherwise specified, and these terms include but are not limited to individual cells, harvested cells, cultures containing cells, and so forth. Furthermore, a particular designation includes the progeny of that originally prepared. It is understood that spontaneous or induced changes can take place in the DNA and morphology of cells over several generations. Progeny which contain such changes are still included within the definition so long as their essential features as related to the invention are maintained. For example, for a hybridoma secreting the monoclonal antibody specific against parathyroid tissue, any descendant of a secreting cell originally identified is included so long as it continues to secrete the antibody with desired characteristics.

For convenience, clones of immortalized cells and the monoclonal antibodies they secrete will be designated by the same name—for example, BB5-M refers both to the antibody and to the cells secreting it.

"Immortalizing cell line" refers to a cell line which can be perpetually (for practical purposes) maintained in cell culture, that is, for an indefinite number of transfers. It also confers this property on the fusion product when fused to an ordinary nontransformed cell line.

B. General Description

Disclosed below are procedures for preparation of monoclonal antibodies specifically immunoreactive with human parathyroid-characteristic antigens, for labeling these antibodies, and for using these labeled antibodies to locate parathyroid tissue in human subjects. Also described are methods of treating hypoparathyroidism by administering the antibodies of the invention, and of treating hyperparathyroidism by administering immunotoxins prepared from these antibodies.

Preparation of Monoclonal Antibodies

In general, the procedure of Kohler and Milstein is adapted to the preparation of the desired antibodies and, if desired, followed by obtaining appropriate switch variants using the method of Dangl, J. L., and Herzenberg, L. A., *J Immunol Meth* (1982) 52:1.

Hybridomas capable of secreting the desired monoclonal antibodies are created by fusing spleen cells or peripheral blood lymphocytes from a mammal immunized with parathyroid tissue to cells of an immortalizing cell line, typically a myeloma line of the same species as that from which the antibody-secreting cell is derived. Convenient myeloma lines are available from mouse and rat, and these mammals therefore make good subjects for production of polyclonal antisera and the immunoglobulin-secreting cells. However, it is understood that any available immortalizing cell line may be used with secreting cells obtained from a compatible species. In addition, certain antibody-secreting cells may be immortalized by viral infection, such as by treating with Epstein-Barr virus. These alternate immortalizing techniques may also be employed to obtain the immortalized immunoglobulin-secreting cells of the invention.

Hybridomas are created by fusing the antibody-secreting cell line with the immortalizing cell line in the presence of an activating agent such as polyethylene glycol. Details of this, now standard, procedure are known in the art and need not be recited here. The critical parameters determining success or failure generally relate to the choice of immortalizing cell lines or method of immortalizing, and to the choice of the population of antibody-producing cells. This latter preparation is, in turn, dependent on the use of the correct immunizing agent for administration to the mammal generating these cells.

In the present invention, homogenates of parathyroid tissue obtained from patients with primary parathyroid hyperplasia are appropriate. The parathyroid tissue is initially physically separated from surrounding foreign contaminating tissue and homogenized in phosphate buffered saline (PBS). The homogenate is then emulsified in Freund's complete adjuvant and injected into suitable host organisms, preferably mice.

In a preferred procedure, isolated spleen cells from the immunized mice are fused with a myeloma line derived from the same species, and the resulting cells grown on selective media. Many readily available myeloma lines are HAT or AH sensitive, that is, they fail to grow on a medium containing hypoxanthine, aminopterin, and thymidine, or on AH medium containing azaserine and hypoxanthine. Both of these media take advantage of the capacity of normal cells to utilize a salvage pathway for DNA synthesis under circumstances where the de novo process is inhibited (in this case, by aminopterin or azaserine). Hypoxanthine and thymidine (or hypoxanthine alone) are requirements for the salvage pathway.

Therefore, only immortalizing cells which are fused to normal cells are capable of survival in this selection medium; unfused immortalizing cells which are HAT or AH sensitive will die. Of course, the normal cells which have not been immortalized by fusion would die anyway. Therefore, only cultures containing fused cells are ultimately available for screening to detect production of the desired antibody.

Cultures of fused cells which survive in selection medium or cells immortalized by other methods are then screened for secretion of antibody having the desired characteristics. The culture media are assayed using immunoreaction-based assays, including, without limitation, Western blot, ELISA, and RIA. The antigen used for this screen must be chosen to insure the correct specificity. Useful in this regard are purified parathyroid homogenates or sections of parathyroid tissue, including those of other species which are suitably cross-reactive. Particularly desirable is screening with the herein-identified parathyroid-characteristic antigen of molecular weight 191 kd. Negative screens are also included to insure parathyroid specificity.

The antibodies from a line identified as secreting the correct antibodies can be recovered from the medium using standard purification techniques if desired. Standard techniques are also available for labeling the isolated antibodies.

For use in the radioimaging method of the present invention, it is desirable to obtain monoclonal antibodies of a class capable of passing through the vascular walls. In the illustration below, the cell line identified initially as secreting the antibodies of desired specificity produced antibodies of class IgM, a pentamer which may cause difficulty in in vivo use due to its relative inability to cross the vascular walls of the circulation system. For such use, it would be preferable to obtain this immunoglobulin in monomeric form. Also, if to be used therapeutically, the functional characteristics of other subclasses may be desired. Techniques for obtaining switch variants are available, as described by Dangl and Herzenberg (supra). These techniques capitalize on the lack of complete monoclonal character of a particular set of progeny from a single ancestor, a consequence of the spontaneous mutation which occurs in the process of cell division at very low frequency, sufficient to generate about 1 descendant out of $10^7$ cells, which, in fact, produces a different class of immunoglobulin. Obtaining "switch variants" is really a process of repeatedly screening populations for the few cells which have the desired property.

In a typical procedure to identify these populations, the hybridoma secreting the surface immunoglobulin of desired specificity is stained with a fluoresceinated or otherwise labeled antiserum specific for the desired isotype. The cells are then sorted on a fluorescence-activated cell sorter (FACS) and the brightest 0.5-1% of the cells are chosen. The dead cells must be gated out with propidium iodide to avoid selecting nonspecifically fluorescent cells. The sorted population is then grown in tissue culture and sorted in the same way to enrich for cells expressing the desired isotype. Several rescreenings may be required to obtain an identifiable population of cells secreting the correct isotype. Cells are cultured from this identified subtype and used to obtain individual colonies.

The selected and screened hybridomas that produce the desired antibodies are grown in vitro or in vivo using standard procedures. The antibodies are isolated from culture media or body fluids, as the case may be, by conventional immunoglobulin purification procedures such as ammonium sulfate precipitation, gel electrophoresis, dialysis, chromatography and ultrafiltration to a purity appropriate to the expected use.

If antigen-specific fragments are desired for use in radioimaging or immunotoxin preparation, the Fab or F(ab')$_2$ fragments may be prepared by standard methods such as those described by Weir, D. M., *Handbook of Experimental Immunology* (3d Ed, 1978) Blackwell Science Publ., Oxford.

Use of Labeled Monoclonal Antibodies in Imaging

Labeled monoclonal preparations are useful in locating parathyroid tissue in candidates for parathyroidectomy. Techniques for labeling antibodies or their sub-fragments are well known in the art, and a variety of labels are used, depending on the purposes for which the immunoglobulins are intended, including fluorescent, chromogenic, and radioactive labels. Typically, for in vivo applications radiolabeled antibodies are preferred, as this permits detection of the internalized antibodies.

A number of radioisotopes are commonly used, including iodine-123, iodine-125, iodine-131, technetium-99, gallium-67, and indium-111. The iodine isotopes are not preferred because they interact with the thyroid gland and may exhibit side effects, although otherwise they are satisfactory. Technetium-99 has a half life of approximately six hours, which is difficult to accommodate to some purposes, and, in particular, may require for use in the method of the invention levels of radiation which are higher than desired. Indium-111, on the other hand, has a half life of three days and appears to be the preferred isotope.

Methods for binding these isotopes to the antibody or a fragment of antibody are understood in the art and include the use of iodination with 1,3,4,6-tetrachloro-3a,6a-diphenylglycocuril (Fraker, P. J., et al, *Biochem Biophys Res Comm* (1978) 80:849-857) and the covalent coupling of a chelating agent capable of binding metal ions such as indium-111, as described by Hnatowich, D. J., et al, *Science* (1983) 220:613-615. The Hnatowich article contains references to still other approaches to labeling proteins. Of course, other iodinating and chelating methods can be used to attach the foregoing isotopes to the antibody or fragment thereof.

The labeled monoclonal preparation is administered to the patient intravenously in an appropriate carrier at a time several hours to 4 days before the tissue is to be imaged. During this period, non-bound fractions are cleared from the body, and the only remaining labeled monoclonal antibodies are those associated with the parathyroid tissue. At this time, the subject is placed in front of a suitable gamma camera to detect the presence of the isotope. This results in a "picture" of the labeled tissue, which can be correlated with known markers on the patient's body to pinpoint the location of the parathyroid for the surgeon.

Use of Monoclonal Antibodies in Treating Parathyroid Secretion Abnormalities

The antibody preparations of the invention are also useful in directly treating patients who have abnormally high or low levels of parathyroid hormone in their systems. Certain of the antibodies per se are capable of effecting increased secretion of parathyroid hormone upon binding to the gland. Conversely, these and other parathyroid-specific antibodies, as well as antigen-specific fragments of these antibodies may also be conjugated to toxic moieties such as, for example, ricin A, diphtheria toxin, abrin, modeccin or bacterial toxins from Pseudomonas or Shigella. Toxins and their derivatives have been utilized to form conjugates with antibodies specific to particular target tissues, often cancer or tumor cells in order to obtain specific toxicity. See, for example, Moolten, F. L., et al, *Immun Rev* (1982) 62:47-72 and Bernhard, M. I., *Cancer Res* (1983) 43:4420. In addition, certain subclasses such as IgG2a and IgG2b are relatively cytotoxic per se.

Conjugation of the toxic and parathyroid specific moieties can be conducted by standard means known in the art. A number of commercially available bifunctional linking agents are available, for example, from Pierce Chemical Company, Rockford, Ill. Such cross-linking agents include, most prominently, heterobifunctional linkers such as N-succinimidyl3-(2-pyridyldithio)propionate (SPDP) which generates a disulfide linkage at one terminus and an amide linkage with an available amino group on the subject molecule at the other. A number of maleimido containing compounds are also available which generate thioethers with available sulfhydryls on the subject molecule, along with an amide at the other terminus, for example, succinimidyl4-(N-maleimidomethyl)cyclo-hexane-1-carboxylate (SMCC). A large number of homobifunctional and heterobifunctional linkers are available and methods for their use are understood in the art.

Administration of the antibodies or immuno-toxins for therapeutic use is most conveniently by an intravenous route, although by proper formulation, additional routes of administration such as intraperitoneal, oral, or transdermal administration may also be used. Methods of formulating compositions for administration to human subjects by an appropriate, selected mode of administration are well understood in the art. For intravenous administration, injectables can be prepared in conventional forms as liquid solutions or suspensions or in solid forms suitable for solution or resuspension prior to injection, or as emulsions. Suitable excipients include, for example, water, saline, dextrose, glycerol, ethanol, Hank's solution, Ringer's solution and the like. In addition these compositions may also contain minor amounts of non-toxic auxiliary substances such as wetting or emulsifying agents, pH buffering agents, and so forth, such as sodium acetate, sorbitan monolaurate, or triethanolamine oleate.

Antibodies useful for enhancing secretion of PTH are those which bind to the 191 kd parathyroid-characteristic antigen. Both BB5-Gl and BB5-M may be used and are preferred. A suitable dosage is in the range of 50 μg–1 mg. Repeated administrations may be necessary, and therefore formulations suitable for self-administration may be desirable.

Administration of the immunotoxins to control hyperparathyroidism uses dosage levels dependent on the toxicity of the conjugated toxin but will generally be in the range of 0.1–1 mg/kg. The immunotoxin will generally be formulated into vehicles for parenteral administration, such as Hank's solution or Ringer's solution in concentrations of about 1 mg/ml to 10 mg/ml to permit the injection of relatively small volumes. Treatment of patients for hyperparathyroidism using these materials will generally be on an acute rather than on a chronic basis, and intravenous injection is entirely satisfactory for this purpose.

Kits

The labeled antibody reagent may be packaged in unit dosage form, including means for administration, such as an injection syringe, if desired.

The unlabeled materials used for direct treatment may also be packaged as kits. In particular, the antibody preparation utilized for inducing increased secretion of parathyroid hormone can be packaged in daily or weekly dosage units in suitable pharmaceutical compositions for self-administration.

C. EXAMPLES

The following examples are intended to illustrate but not limit the invention.

EXAMPLE 1

Preparation of Hybridoma BB5

Adult Balb/C mice were immunized intraperitoneally with a homogenate of parathyroid tissue which had been obtained from patients with primary parathyroid hyperplasia, separated from surrounding tissue, homogenized in PBS, and emulsified in Freund's complete adjuvant. Several days later, the mice were sacrificed, and the spleen cells fused with the non-secreting mouse myeloma line SP-2/O-Ag14 using the standard techniques of Kohler and Milstein. After growth on HAT selective media, supernatants from the hybridoma cultures were screened for parathyroid binding using a standard indirect immunofluorescence assay. The assay employs frozen sections of human parathyroid glands which had been cut into 0.2μ sections and immediately fixed in absolute alcohol. The sections were incubated with supernatant, washed, and then incubated with a mixture of goat anti-mouse IgM and goat anti-mouse IgG, which antibodies had been conjugated with fluoroscein isothiocyanate (FITC). The sections were examined microscopically for fluorescence binding.

Cultures with supernatants which bind specifically to the parathyroid tissue were cloned in soft agar and retested using the parathyroid sections and negative screens with sections of thyroid and tonsil.

In more detail, the alcohol treated sections were incubated for 30 min at 4° C. with 1:10 dilutions of hybridoma supernatant, washed, and incubated for 30 min at 4° C. with a 1:50 dilution of the FITC conjugated goat anti-mouse antibodies (Tago, Inc.). The sections were washed again, and examined with a fluorescence microscope.

Hybridoma BB5-M supernatant binds parathyroid tissue sectioned in this way but does not bind to sections of thyroid or tonsil. The BB5-M cell line was cloned several times in soft agar and the antibody was produced by culturing in serum-free medium. The antibody was shown to be IgM (see below) and was purified by subjecting the supernatant to affinity chromatography using Sepharose 4B coupled to M58.6, a rat anti-mouse IgM monoclonal antibody to obtain a 90–95% pure preparation, as determined by SDS-PAGE.

EXAMPLE 2

Characterization of BB5-M Antibody

The secreted antibodies from BB5-M media bound each of 15 different human parathyroid frozen section specimens tested and four preparations of dispersed human parathyroid cells. They cross-reacted with rhesus monkey, pig-tail monkey, and mongrel dog parathyroid tissue, weakly with bovine parathyroid tissue, and not at all with rabbit or rat parathyroid glands. The specificity of BB5-M for human parathyroid appears complete; cross-reactivity was not obtained for any other tissue tested. Tissues tested include human thyroid, tonsil, thymus, lymph nodes, spleen, salivary gland, adrenal gland, pancreas, islets, pituitary gland, testis, pineal gland, pheochromocytoma, esophagus, liver, kidney, lung, heart atrium, heart ventricle, gall bladder, duodenum, gastric antrum, cerebrum, cerebellum, spinal cord, and hypothalamus, most of the same tissues in monkeys, and thyroid and lymph node tissues from dogs.

The isotype was determined to be IgM,k by radioimmunoassay, described by Perlmutter, R. M., et al, *J Immunol* (1978) 121: 566.

EXAMPLE 3

Antigen Characterization

The antigen to which BB5-M antibody was bound was identified by Western blot and by subjecting an immunoprecipitated homogenate of surface $^{125}$I-labeled parathyroid tissue to SDS-PAGE and autoradiography.

Parathyroid tissue was obtained from patients with primary parathyroid hyperplasia, and the tissue was minced and digested with collagenase/DNase as described by Brown, B. M., et al, *Endocrinol* (1976) 99: 1582. The dispersed cells were cultured for 48–72 hours to allow regeneration of any cell surface determinants which were removed during digestion, since protease impurities in the collagenase preparation may cause digestion. The cells were then surface-iodinated according to the method of Markwell, M. A. K., et al, *Biochem* (1978) 17: 807. The cells were lysed and the cell surface macromolecules immunoprecipitated with BB5-M which had been indirectly coupled to staphylococcus with a rabbit anti-mouse IgM antiserum. The immunoprecipitate was then analyzed on SDS-PAGE and autoradiographed.

Under non-reducing conditions, the major species immunoprecipitated with BB5-M migrated as a 191 kd single polypeptide protein with two minor single-stranded precipitated proteins of 162 kd and 129 kd. Under reducing conditions (BME) the protein migrated as corresponding 171 kd, 140 kd, and 110 kd bands. The antigens precipitated do not appear to be secreted by the target cells; BB5-M thus binds to a protein permanently associated with the gland.

EXAMPLE 4

Preparation of IgG

Using the method of Dangl and Herzenberg (supra), a switch variant was obtained from BB5-M which secretes an IgGl antibody specific against parathyroid tissue. This hybridoma/immunoglobulin was designated BB5-Gl. The specificity of this variant was confirmed in a manner described in Example 2 above. The IgGl antibody was purified from the supernatant by affinity chromatography using Sepharose 4B coupled to 187.1, a rat anti-mouse $\kappa$ light chain monoclonal antibody.

EXAMPLE 5

Radiolocalization Studies of Parathyroid Implants in Nude Mice

Fresh parathyroid tissue obtained from patients undergoing parathyroidectomy was minced and implanted into the posterior thigh muscles of nude Balb/C mice obtained from Sasco, Inc., O'Fallon, Mo. and from St. Louis Children's Hospital, St. Louis, Mo. using microsurgical techniques. Control human thyroid tissue or breast tissue was transplanted into the contralateral thigh. After 2-3 weeks to allow the parathyroid tissue to form a neovasculature, the mice were injected with purified radiolabeled BB5-Gl.

General Method

Mice containing the implants were injected with $^{125}$I-labeled BB5-Gl. At various times, the mice were sacrificed and the grafts removed, weighed, and counted to determine the percent of injected dose per gram of tissue in the implant (% ID/gm). Some implants were fixed, sectioned, and autoradiographed by dipping the slides in photographic emulsion. After several days exposure, the slides were developed, stained with eosin and hematoxylin, and examined under a microscope. Other tissues were compared to assess nonspecific uptake. Specific binding of $^{125}$I-labeled BB5-Gl to the human parathyroid was demonstrated; control human breast tumor BT20 implants showed no uptake of the antibody. Clearance of the antibody was consistent with the normal half life of IgGl.

Determination of Dose

Injections were made using 15 $\mu$g, 50 $\mu$g, or 150 $\mu$g of $^{125}$I-labeled BB5-Gl (activity) to 3 groups of 3 mice each, and the specific binding measured by counting the radioactivity of various tissues after four days. The parathyroid tissue showed 11%, 18%, and 7% ID/gm for dose levels of 15 $\mu$g, 50 $\mu$g, or 150 $\mu$g, respectively. Antibodies from all three dosage levels remained in the blood after four days, but did not bind to other tissues, as other tissues exhibited only background levels of radiation.

Time Dependence

The time course of labeling was determined by using 3 groups of 3 mice injected with 50 $\mu$g of labeled antibody, sacrificing the animals at days 1, 4, and 7, and counting various tissues, as described. There was a linear increase of binding to parathyroid with time over this period reaching 26% ID/gm after 7 days, and the blood clearance was determined to be consistent with this pattern. Highest levels of the antibody were in the blood of animals sacrificed after 1 day, lowest in the blood of those sacrificed at day 7.

Tissue Sections

Figure 1:
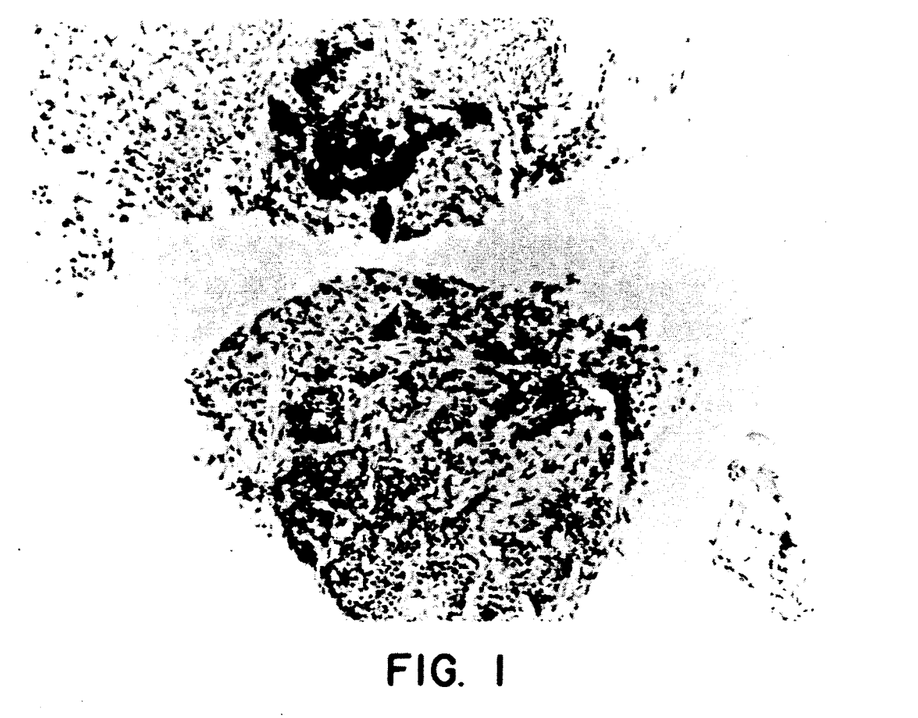
FIGS. 1 and 2 are photomicrographs, taken in opposite phases, of parathyroid transplants in nude mice after the mice were injected with BB5-G1 conjugated to I-125.
Figure 2:
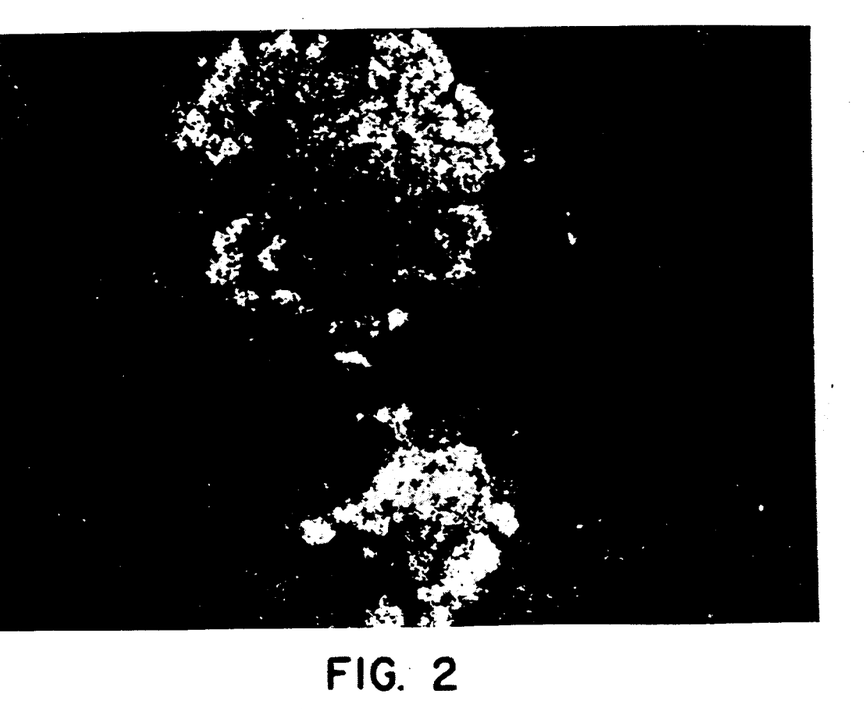

Parathyroid grafts determined to contain antibody in the previous paragraphs were excised with surrounding muscle and formalin-fixed, paraffin-embedded, and sectioned. Slides were autoradiographed by dipping in a Kodak nuclear track emulsion exposed for 14-21 days, developed and stained with hematoxylin. The presence of antibody was shown by the appearance of silver grains over the cells. FIGS. 1 and 2 represent bright field and dark field micrographs of the fixed tissue. The parathyroid tissue is clearly defined by the antibody binding using either of these phases. The highest degree of binding is to the periphery, away from the central fibrotic area.

Indium-111 Label

In addition, 4 mice administered 50 $\mu$g of $^{111}$In-labeled BB5-Gl were sacrificed on day 4 and tissues analyzed for % ID/gm. Parathyroid tissues showed a % ID/gm of almost 65%, whereas other tissues showed only nonspecific binding.

EXAMPLE 6

Stimulation of Parathyroid Hormone Secretion

Bovine and human parathyroid cells were prepared by the collagenase/DNase method of Brown, B. M., et al, (supra). Human cells were used the same day as acutely dispersed cells; bovine cells either were used the same day or were cultured in suspension for 1-2 days in equal parts Hamm's F12 and Dulbecco's modified Eagle medium containing 4% calf serum and 5 $\mu$g/ml insulin, as described below.

In an initial experiment acutely dispersed bovine cells were treated with 5000 ng/ml BB5-M monoclonal antibody at both high and low calcium concentrations and the secretion of parathyroid hormone (PTH) was measured in units of ng PTH/$10^5$ cells/hr by radioimmunoassay using labeled anti-serum raised against the carboxy terminal fragment of PTH containing amino acids 35-84. The antiserum thus detects both intact PTH and the C-terminal fragment.

Table 1 shows the effect of 5000 ng/ml BB5-M on the secretion of PTH at high and low calcium concentrations.

TABLE 1

| [Ca$^{+2}$] | Control | BB5-M | HPC$\mu$2-M |
|---|---|---|---|
| 0.5 mM | 8.4 ± 1.1 | 16.4 ± 2.3 | 8.6 ± 1.5 |
| 2.0 mM | 4.7 ± 0.5 | 8.8 ± 2.3 | 4.8 ± 0.9 |

Table 1 shows that both at low and high calcium concentrations, BB5-M almost doubles the level of secretion of PTH, while a control antibody, HPC$\mu$2 has no detectable effect. The values shown are the mean ± SD for three separate cell preparations.

Similar results were obtained for acutely dispersed human parathyroid cells as shown in Table 2. The dispersed human parathyroid preparations were subjected to 5000 ng/ml BB5-M in the presence of 0.5 mM calcium ion and PTH secretion again expressed as ng PTH/$10^5$ cells/hr.

TABLE 2

| Cell Prep | Control | BB5-M | HPCμ2-M |
|---|---|---|---|
| 1 | 11.4 ± 1.3 | 19.6 ± 2.6 | 11.2 ± 1.5 |
| 2 | 17.3 ± 2.1 | 24.9 ± 2.8 | 16.8 ± 2.4 |
| 3 | 10.4 ± 1.7 | 20.7 ± 2.1 | 10.6 ± 1.9 |

Again a reproducible stimulation of PTH secretion occurs. The values are for 5 replicate incubations of the individual preparations.

Figure 3:
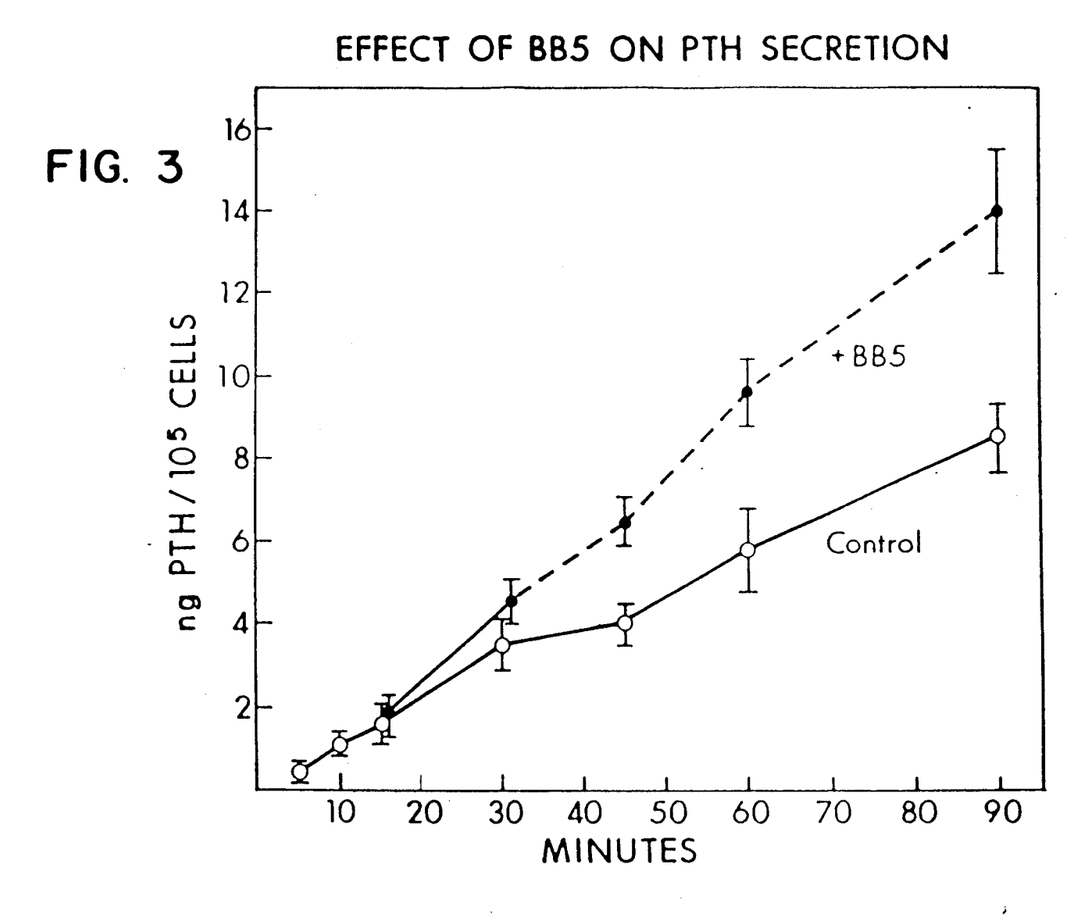
FIG. 3 shows the time dependence of PTH secretion stimulation by the monoclonal antibodies of the invention.

Unlike β agonist drugs such as isoproteronol, the effect of BB5-M shows a linear time dependence as illustrated in FIG. 3. Acutely dispersed bovine cells in 0.5 mM calcium ion were treated with 5000 ng/ml BB5-M (or control cells were untreated) and the supernatants were assayed for ng PTH per $10^5$ cells as described above. After a 15 min lag time, the secretion curve for the BB5-M treated cells diverges from that for controls to show the expected increased levels of secretion. Thus, results as shown in Tables 1 and 2 can validly be based on hourly secretion rate.

Figure 4:
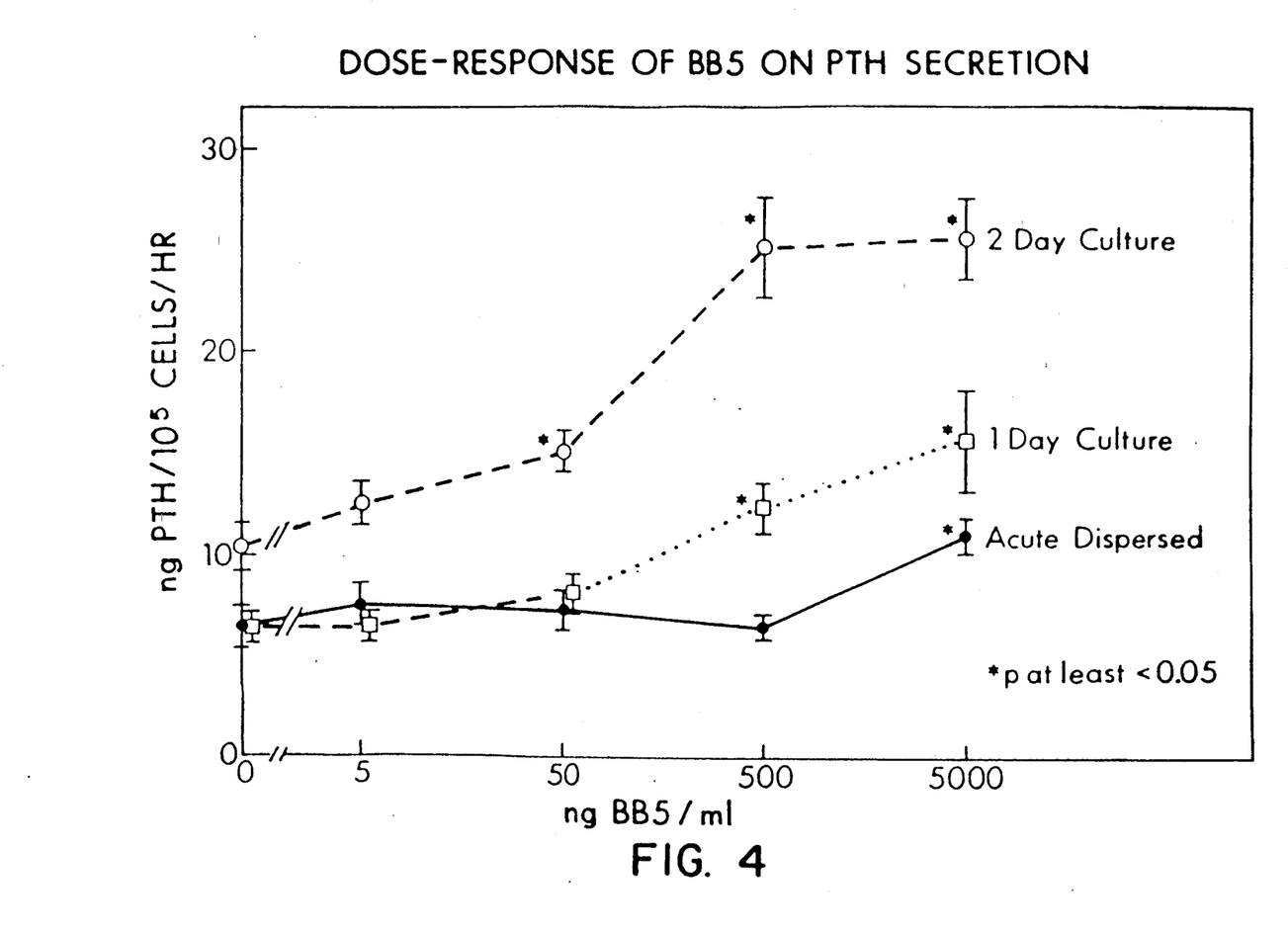
FIG. 4 shows the dose-response curve for acutely dispersed bovine parathyroid cells treated with BB5-M antibodies.

A dose response curve of the effect of BB5-M on PTH secretion was determined for the acutely dispersed bovine cells, and for dispersed bovine cells after culturing for 1 or 2 days to regenerate the surface markers. The results are shown in FIG. 4. As expected, higher dosage levels of BB5-M are more effective in enhancing secretion of PTH; in addition lower dosage levels are required for cultured cells which have had the opportunity to generate the surface markers responsive to BB5-M. The effect of BB5-M on dispersed cells was not apparent until a dosage level of 5 μg/ml was supplied; conversely, comparable effect on secretion of PTH from 2 day cultured cells was obtained using a dosage of only 50 ng/ml; and for 1 day cultured cells using 500 ng/ml. The results shown in FIG. 4 are for 0.5 mM calcium ion concentration; similar results were obtained but at 40% reduced PTH secretion levels, in the presence of 2 mM calcium ion.

Further characterization of the nature of the stimulation was tested by examining the effect of the antibody on cyclic AMP levels and on the nature of the PTH secreted.

Cyclic AMP was determined by extraction from cell pellets using 0.1N HCl and determining cyclic AMP concentration in the extract by radioimmunoassay. The assay was performed after acetylating both cyclic AMP standards and the extracts. The anti-sera used in the assay were raised against acetylated cyclic AMP. Dispersed bovine parathyroid cells in the presence of 0.5 mM calcium ion and with or without 5000 ng/ml BB5-M were assayed for cyclic AMP content at intervals up to 90 min after treatment with BB5-M. The level of cyclic AMP in both control and BB5-M treated cells was approximately 400 fmoles/$10^5$ cells and remained unchanged over this time period.

In addition, the effect on the secretion level of the intact and the carboxy terminal portion of the PTH was explored. Normally, at low calcium concentrations, the parathyroid gland secretes about 50% of the PTH synthesized as intact PTH and retains about 10% of the PTH formed. 40% of the PTH synthesized is degraded and some is secreted as the carboxy terminal portion of the peptide (amino acids 35–84).

Acutely dispersed bovine cells in 0.5 mM calcium ion were treated with 5000 ng/ml BB5-M or untreated as controls and the supernatants were examined after 1.5 hr using polyacrylamide gel electrophoresis in 8M urea, pH 4.5.

Figure 5:
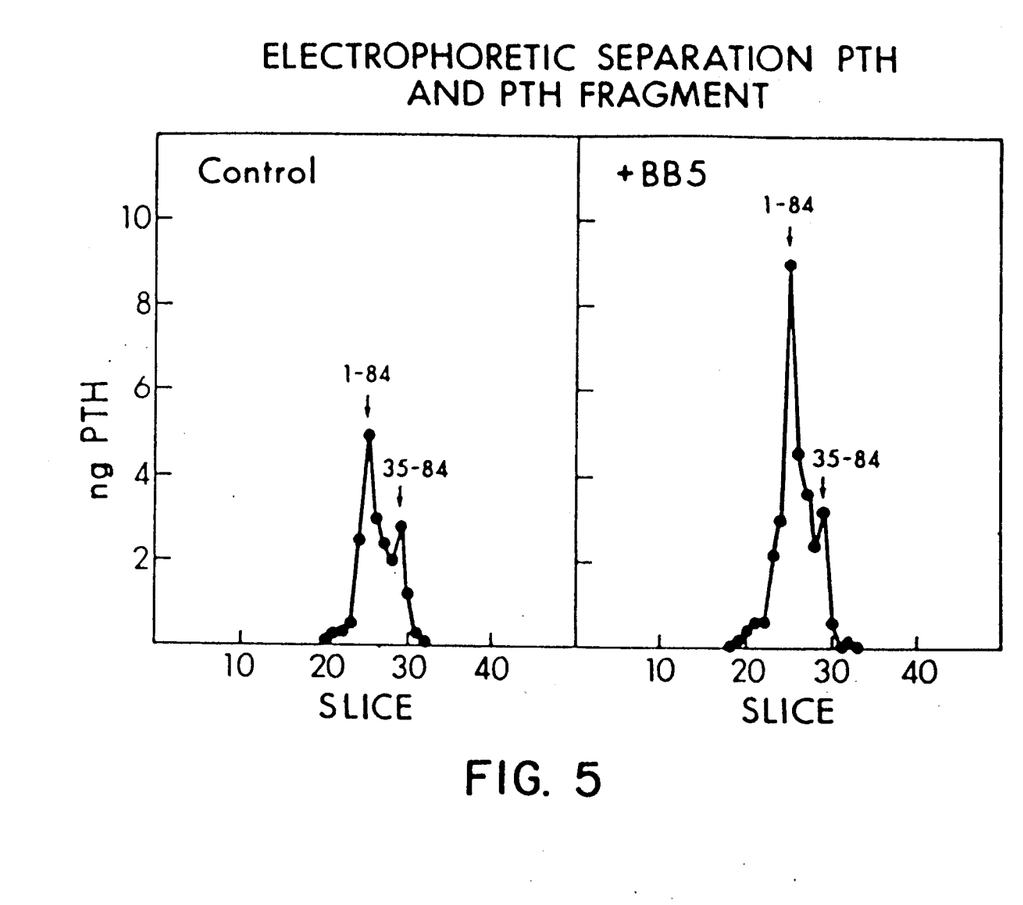
FIG. 5 shows the effect of BB5-M antibody treatment on the secretion of intact parathyroid hormone (PTH) and of the C-terminal fragment containing amino acids 35-84 of PTH.

PTH protein was located on the segmented gel by radioimmunoprecipitation with anti-sera raised against the C-terminal portion of PTH. The results are shown in FIG. 5. It is apparent that the stimulation effect of the BB5-M is directed specifically to the intact protein; the level of C-terminal fragment secreted is not changed.

We claim:

1. Monoclonal antibodies specifically immunoreactive with a human parathyroid tissue-specific antigen not secreted by said gland, wherein said antibodies are not immunoreactive with other human tissue, and
   wherein said antigen has an apparent molecular weight of 191 kd (non-reduced) and an apparent molecular weight of 171 kd (reduced) on SDS-polyacylamide gel electrophoresis and
   wherein said antigen is found on the surface of parathyroid tissue.

2. The antibodies of claim 1 which are of class IgM.

3. The antibodies of claim 1 which are of class IgG1.

4. Subfragments of the antibodies of claim 1 which retain antigen specificity.

5. The subfragments of claim 4 which are Fab or F(ab')$_2$ subfragments.

6. An immortalized cell line which secretes monoclonal antibodies of claim 1.

7. The immortalized cell line of claim 6 which is a hybridoma.

8. The hybridoma of claim 7 which is prepared by fusing blood lymphocytes or spleen cells from mice immunized with isolated human parathyroid tissue with a murine myeloma line.

9. The monoclonal antibodies of claim 1 covalently bound to label.

10. The subfragments of claim 4 covalently bound to label.

11. The monoclonal antibodies of claim 9 wherein the label is radioactive.

12. The subfragments of claim 10 wherein the label is radioactive.

13. The monoclonal antibodies of claim 11 wherein the label is I-125, In-111, or Tc-99.

14. The subfragments of claim 12 wherein the label is I-125, In-111, or Tc-99.

15. The monoclonal antibodies of claim 1 wherein said antibodies, when bound to the parathyroid gland, enhance the secretion of parathyroid hormone.

* * * * *